United States Patent [19]

Metz

[11] Patent Number: 5,336,211

[45] Date of Patent: Aug. 9, 1994

[54] EXTERNAL MALE CATHETER, APPLICATOR AND METHOD OF USE

[75] Inventor: Michael Metz, Chicago, Ill.

[73] Assignee: Hollister Incorporated, Libertyville, Ill.

[21] Appl. No.: 964,743

[22] Filed: Oct. 22, 1992

[51] Int. Cl.$^5$ ............................................. A61F 5/44
[52] U.S. Cl. ................................ 604/352; 604/349; 604/346; 128/844
[58] Field of Search ................. 602/58, 901; 128/844; 604/317, 346, 347, 349, 352

[56] References Cited

U.S. PATENT DOCUMENTS

| | | | |
|---|---|---|---|
| 3,835,857 | 2/1973 | Rogers et al. | 128/295 |
| 3,863,638 | 2/1975 | Rogers et al. | 128/295 |
| 4,187,851 | 2/1980 | Hauser | 128/295 |
| 4,378,018 | 3/1983 | Alexander et al. | 128/295 |
| 4,540,409 | 9/1985 | Nystrom et al. | 604/349 |
| 4,581,026 | 4/1986 | Schneider | 604/352 |
| 4,626,250 | 12/1986 | Schneider | 604/352 |
| 4,840,187 | 6/1989 | Brazier | 128/844 |
| 4,934,382 | 6/1990 | Barone, Jr. | 128/844 |
| 5,070,890 | 12/1991 | Papurt | 128/844 |

FOREIGN PATENT DOCUMENTS 2120102 11/1983 United Kingdom .

Primary Examiner—David Isabella
Assistant Examiner—Paul Prebilic
Attorney, Agent, or Firm—Tilton, Fallon & Lungmus

[57] ABSTRACT

The combination of an external male catheter and an applicator to facilitate properly fitting the catheter on a patient, as well as the method for doing so, are disclosed. The catheter is preferably of the type disclosed in U.S. Pat. No. 4,540,409 and the applicator takes the form of a relatively rigid open-ended tube and a flexible tubular drawsleeve formed of substantially non-stretchable material that slides easily against the surfaces of the tube. The drawsleeve includes a first portion disposed within the applicator tube and surrounding the neck and drainage tube portions of the catheter therein, a second portion extending a substantial distance outwardly (axially) from the interior of the tube at one end thereof, and a third portion interposed between the outer surface of the tube and the cylindrical body of the catheter. A user applies the catheter by gripping and pulling the exposed second portion of the drawsleeve to extract the drawsleeve from one end of the applicator tube while the interior surfaces of the catheter sheath at the opposite end of the applicator tube are in contact with the penis.

18 Claims, 2 Drawing Sheets

EXTERNAL MALE CATHETER, APPLICATOR AND METHOD OF USE

BACKGROUND

The use of external catheters for male urinary drainage systems is well known, as disclosed in U.S. Pat. Nos. 4,378,018, 4,187,851, 3,863,638 and 3,835,857. Essentially, such a system comprises an elastic sheath adapted to fit over the user's penis, the sheath having an outlet at its distal end connected to a tube leading to a suitable collection receptacle. The sheath includes a cylindrical body portion that fits over the penile shaft, a tapered neck portion that functions as a surge chamber near the distal end of the sheath, and a reduced drainage tube portion that extends beyond the neck portion. In a preferred construction, the sheath also includes an inner sleeve portion for sealingly (but non-adhesively) engaging the head or glans of the penis as disclosed in U.S. Pat. Nos. 4,581,026 and 4,626,250.

External catheters also quite commonly have an annular layer of pressure-sensitive adhesive on the inner surfaces of their cylindrical portions to retain the sheaths in place. Whether adhesive-coated or not, such catheters are usually marketed in rolled form with instructions that the sheaths be unrolled during application in essentially the same manner as a prophylactic condom.

Experience has revealed that such an application procedure is more difficult than it sounds. Orienting and unrolling a sheath with respect to a flaccid (and possibly retracted) penis is difficult even for a patient that retains manual dexterity and is capable of applying such a product to himself; it is obviously more difficult for a nurse or other attendant who lacks the tactile feedback that would assist a patient in carrying out the procedure on himself. The problems are compounded by the fact that a nurse undertaking such a procedure would normally wear surgical gloves and, should such gloves happen to contact the adhesive of the catheter as it is being unrolled, the gloves and catheter may adhere strongly to each other. Experience indicates that problems of applying such a catheter tend to be reduced if a nurse holds the penis in one hand and directs it into the opening of the rolled catheter held in the other, and then, immediately after commencing the unrolling operation, externally grips the sheath-covered glans and stretches or extends the penis as the unrolling operation is continued. It is believed, however, that nurses sometimes fail to perform such procedures completely, or with sufficient patience and care, because they are concerned about possible discomfort or injury to the patient, or are rushing to perform other healthcare duties, or simply because they find themselves uncomfortable making such direct and extended contact with the limp penis of an incontinent patient. Often the result is that such an external catheter is improperly or incompletely applied, causing discomfort and possible injury to the patient and resulting in leakage of urine when the drainage system is in use.

Other systems have been proposed in the past that utilize non-rolled sheaths and would not present the unrolling problems described above. Co-owned U.S. Pat. No. 4,540,409 discloses a catheter which has its cylindrical portion externally supported by a rigid and slightly tapered applicator tube. The neck and drainage tube portions of the catheter are reverted and extend through the interior of the tube. In applying the catheter, the entrance opening of the tube is directed towards the glans and the user grips the outlet tube section of the catheter to restrain that section, or even exerts a gentle pulling force, while at the same time urging the applicator tube in the direction of the penis. It has been found, however, that static friction between the applicator tube and the portion of the catheter stretch about it is not easily broken. Pushing the applicator tube more forcefully against the patient in order to overcome such frictional resistance may not only cause discomfort and possible injury to the patient but is unlikely to be effective because of the flaccidity of the target. Applying pulling force to the outlet tube portion of the catheter in an effort to break such static friction tends to have an opposite effect; the catheter simply stretches more tightly into engagement with the surfaces of the applicator tube at and about its entrance opening.

U.S. Pat. No. 4,840,187 discloses a sheath and applicator tube combination in which a liner casing of netting material is interposed between the tube and sheath to reduce static and sliding friction. The applicator tube is closed at one end and the netting is internally secured to the tube at that end. Inversion of the sheath is produced by pushing the sheath-covered open end of the applicator tube against the glans, although side window openings in the applicator tube do allow the user to grip and guide the distal portion of the penis (and the sheath liner casing covering it) into the interior of the tube.

British patent GB 2,120,102B discloses a more complex device in which an applicator tube is provided with a slidable internal tube 14 and a slidable external ring 15 connected to opposite ends of a woven liner. Use of the device is described as requiring the user to steady the penis with one hand while at the same time pulling draw pin 16 axially to shift the inner sliding tube 14 within support tube 11 to evert both the woven liner and the sheath carried by it.

While the use of a liner has been found to reduce static and sliding friction, those devices identified above which utilize such liners are still relatively complex in structure and operation and may be difficult to use effectively. In general, their recommended usage requires the operator to hold, grip, or guide the penis during sheath application, a contact that is often considered objectionable and may not produce the desired results.

SUMMARY OF THE INVENTION

This invention is concerned broadly with a combination of an external male catheter and a tubular applicator which encloses a portion of a substantially non-stretchable drawsleeve for applying the catheter to the penis. While finger contact with the penis may be made at an initial stage in the application procedure to insure that the penis and the applicator are properly oriented with respect to each other, even such limited contact is seldom necessary. Later, during the actual application of the elastic sheath to the penis, both hands are in contact not with the penis but with the applicator (and possibly with a portion of the sheath carried by it), one hand being used to grip and pull the end portion of the drawsleeve that projects through the open rear end of the applicator tube and the other hand being used to direct the applicator tube, maintaining its entrance opening in close proximity to the penis and, if desired, urging the cylindrical body portion of the sheath towards that entrance opening.

The invention is particularly effective when used with an external catheter that has an inner sleeve 13 of the type disclosed in aforementioned U.S. Pat. No. 4,540,409, for reasons described in detail hereinafter. It is also desirable if the catheter sheath is of the adhesive-coated type, since the combination of this invention allows such a catheter to be applied to a patient with little or no risk that the pressure-sensitive adhesive coating of the sheath will be contacted by the user's fingers.

Briefly, the combination takes the form of an applicator tube supporting an external male urinary catheter with the distal portion of the catheter (which includes its tapered neck section and its outlet section) disposed within the tube and its cylindrical body section everted and extending externally about the tube. A flexible, tubular, and longitudinally non-stretchable drawsleeve is interposed between the inner and outer surfaces of the tube and the catheter to reduce static and sliding friction and, in particular, to provide means that may be gripped directly between a user's fingers of one hand to pull the drawsleeve from the rear end of the tube while the tube is being held and directed by the user's other hand. The pulling force exerted on the drawsleeve causes that portion of the drawsleeve external to the rigid applicator tube to be reverted and pulled into and through the tube and, at the same time, causes the cylindrical body portion of the catheter to assume its final reverted position about the penile shaft.

Since an adhesive-coated catheter is not supported in rolled condition upon the applicator tube, at least in the sense that inner and outer surfaces of the sheath are in direct concentric contact with each other, the outer surface of the sheath does not require a release coating of the type disclosed in prior patents such as U.S. Pat. Nos. Re. 33,206 and 4,581,026. A silicone release coating is typically applied to the outer surface of a conventional catheter while the release agent is in a dissolved state, and the solvents that have been commonly used in the past may present environmental concerns. Those concerns are eliminated by the combination of this invention because no such release coating is required.

Other features, advantages, and objects of the invention will become apparent from the specification and drawings.

DRAWINGS

DETAILED DESCRIPTION OF PREFERRED EMBODIMENT

Figure 1:
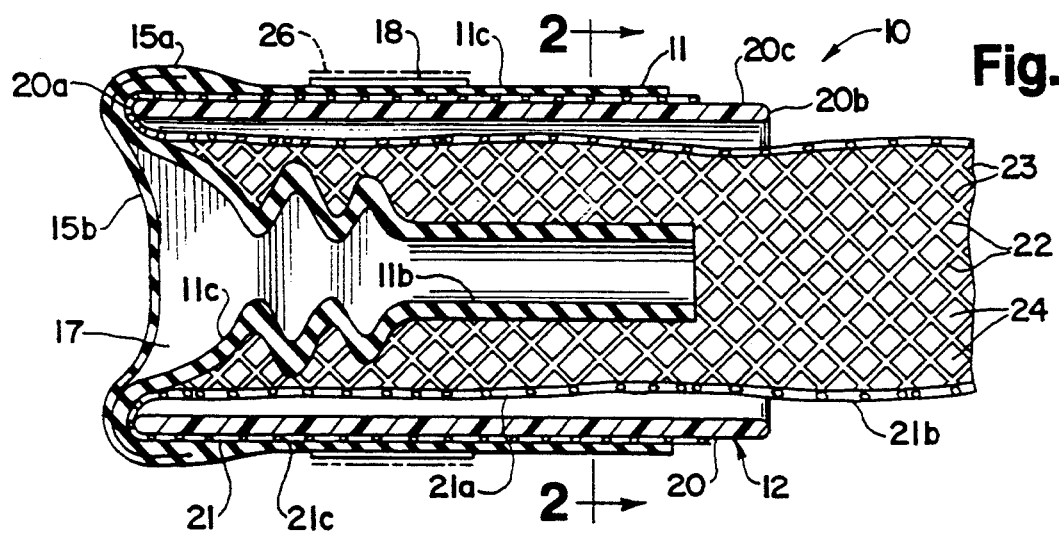
FIG. 1 is a longitudinal cross sectional view of a catheter and applicator combination constituting a preferred embodiment of this invention.

Referring to the drawings, the numeral 10 generally designates the combination of an external male catheter 11 and an applicator 12. The catheter may be an adaptation of a conventional external catheter of the type disclosed, for example, in U.S. Pat. Nos. 4,378,018 (FIG. 7) and 4,187,851 (FIG. 3); however, a catheter having the features disclosed in co-owned U.S. Pat. Nos. 4,581,026 and 4,540,409 is believed particularly desirable because of its inner sleeve construction and the presence of an internal band or zone of pressure-sensitive adhesive.

Figure 7:
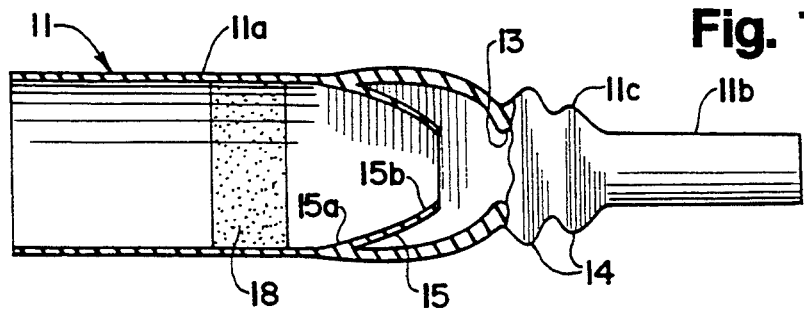
FIG. 7 is a longitudinal sectional view of a catheter as used with the applicator tube and drawsleeve of this invention.

Catheter 11, shown most clearly in FIG. 7, is formed of soft, highly elastic, natural or synthetic rubber. Natural latex is preferred but other elastomers having similar properties, such as silicone rubber, may be used. The catheter comprises a sheath having an elongated cylindrical section 11a, a reduced outlet section 11b, and a tapered neck section 11c disposed therebetween. The wall thickness of the cylindrical section 11a is substantially less than that of the neck and outlet sections. For example the cylindrical section may have a wall thickness within the general range of 0.006 to 0.010 inches and, in general, is too thin or limp to retain a cylindrical configuration without support. In contrast, the wall thicknesses of the outlet and neck sections may be 0.050 inches or more and are generally great enough so that such sections will retain the configurations shown in the absence of distorting forces and will spring back into the illustrated shapes when distorting forces are removed.

At its forward or distal end, the neck section 11c is provided with a rounded taper leading to a reduced opening 13. The outlet section 11b that merges with the tapered neck section 11c is provided with a plurality of convolutions or annular enlargements 14. Two such convolutions of graduated size are depicted, their purpose being to permit greater stretchability, bending, and twisting of the outlet section when the device is in use, and to do so with less chance that kinking or obstruction of the lumen might occur. Also, since the interior of the outlet section is enlarged at such convolutions, convolutions increase the fluid capacity of that section and, along with the neck section, provide a reservoir for accommodating surges of fluid when the catheter is in use.

An inner sleeve section 15 has a proximal end portion 15a that merges smoothly with the distal end of the sheath's cylindrical body section 11a and an elongated distal end portion 15b disposed within the sheath's neck section 11c. The distal portion 15b tapers forwardly and inwardly, terminating in a reduced distal opening 16 that is spaced well behind (i.e., proximal to) opening 14. The setback also results in the provision of an annular and axially-elongated expansion space 17 between the outer surface of the sleeve's distal end portion 15b and the inner surface of neck section 11c. The wall thickness of the sleeve may be varied but, to insure conformability, good sealing properties, and wearer comfort, such thickness should approximate that of the relatively thin cylindrical body section 11a. Thus, both the cylindrical body section 11a and the inner sleeve 15 should appear as thin, limp, highly stretchable membranes, in contrast to the outlet and neck sections 11b and 11c with their shape-retaining properties.

In the preferred embodiment disclosed herein, the catheter or sheath 11 is also provided with an internal adhesive coating or band 18 (FIG. 7). The adhesive zone is located within the cylindrical section 11a of the sheath behind inner sleeve 15. While the adhesive coating might conceivably extend the full length of the cylindrical section 11a, it is believed preferable to provide the adhesive zone in the form of a narrow but continuous band located within the distal portion of the sheath's cylindrical section 11a. The adhesive coating may be composed of any suitable medical-grade pressure-sensitive adhesive of a type well known in the art; a hypoallergenic acrylic adhesive is believed to be particularly effective.

Applicator 12 comprises two components: a relatively rigid applicator tube 20 and a flexible, tubular drawsleeve 21. Tube 20 is generally cylindrical in shape and is open at both its proximal and distal ends 20a and 20b, respectively. The edges of the tube at the proximal end 20a are rounded (when viewed in longitudinal section) and, if desired, the edges at the opposite end may be similarly formed. Tube 20 may be composed of any of a wide variety of generally stiff materials, a relatively rigid polyolefin such as polypropylene or high-density polyethylene being found particularly effective. Other polymeric materials having similar properties may also be used.

Figure 3:
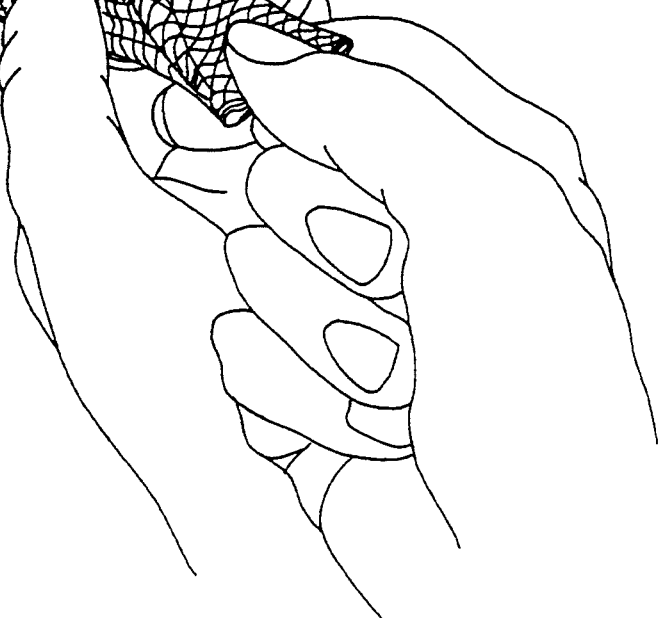
FIG. 3 is a perspective view of the catheter/applicator combination as it would be held by a user for application of a catheter to a patient.
Figure 4:
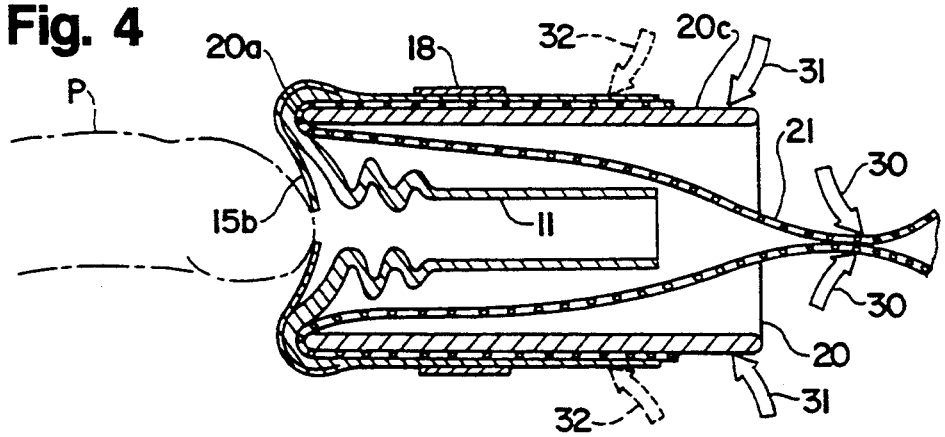
FIG. 4 is a longitudinal sectional view showing a first stage in the application of a catheter sheath.

The length of applicator tube 20 is substantially less than that of elastic sheath 11. The outside diameter of the applicator tube should be slightly greater than the maximum inside diameter of the sheath, particularly the cylindrical body section 11a thereof, in an unstretched state. Referring particularly to FIGS. 1 and 4, it will be observed that the length of the applicator tube is preferably greater than the length of the sheath's cylindrical body section 11a so that when the cylindrical body section is externally supported upon the smooth outer surface of the applicator tube 20, an annular portion 20c of the tube's outer surface adjacent distal end 20b is exposed and may be gripped between the fingers during use of the device as depicted in FIG. 3.

The tubular drawsleeve 21 has an inside diameter (when supported in cylindrical configuration) slightly greater than the outside diameter of rigid applicator tube 20 and has a length considerably greater than that of the sheath 11 and much greater than (at least twice as long as) the length of the applicator tube. In the embodiment illustrated, the drawsleeve is composed of an open mesh of flexible, interconnected polymeric fibers or filaments. Two sets of such fibers 22 and 23 intersect to provide a multiplicity of mesh openings 24 with the parallel fibers of each set extending in directions that are not perpendicular to, and preferably not parallel with, the longitudinal axes of the applicator tube and drawsleeve. As a result, the drawsleeve may slide smoothly over the rounded edges at the entrance or proximal end 20a of tube 20 without a ratcheting action that might otherwise occur if the fibers of either set extended in a plane normal to the axis of the tube. The smooth fibers of the drawsleeve may be formed of any material that is substantially non-stretchable in response to forces of a magnitude that would be expected to arise during use of the product and that has a relatively low coefficient of friction with respect to the material of the applicator tube. A nylon (polyamide) mesh is believed suitable, and particularly effective results have been obtained utilizing a mesh formed of a polyolefin such as polypropylene or polyethylene. In particular, the frictional resistance between the drawsleeve 21 and the smooth surfaces of applicator tube 20 should be substantially less than the frictional resistance between the drawsleeve and the material of catheter sheath 11.

Figure 2:
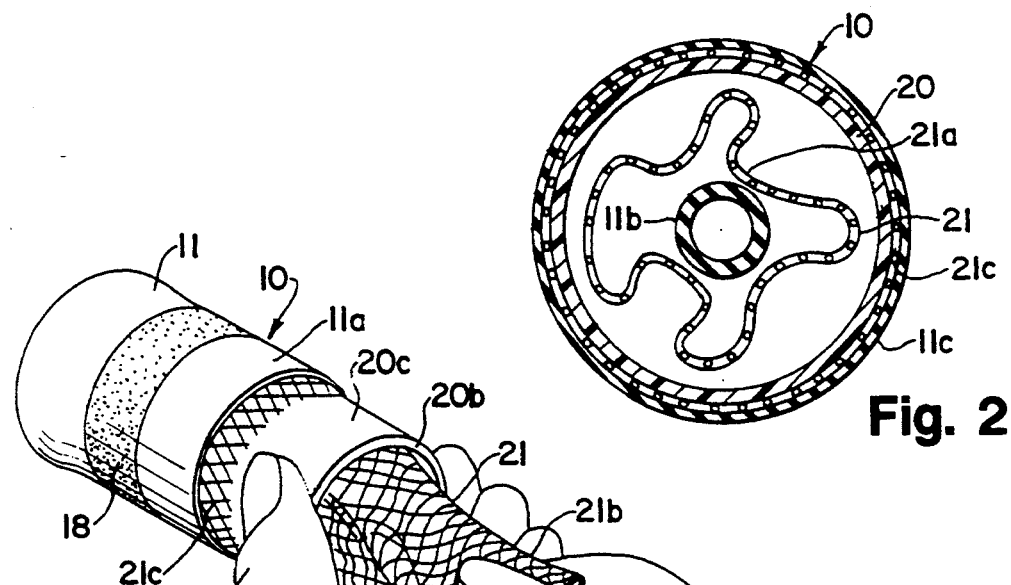
FIG. 2 is a cross sectional view taken along line 2—2 of FIG. 1.

FIGS. 1 and 2 depict the preferred catheter/applicator combination in a form in which it would be made available to users. The catheter sheath 11 has its neck and outlet sections extending axially within applicator tube 20. The neck section 11c extends outwardly through the entrance opening at the tube's first or proximal end 20a and is reverted so that the cylindrical section 11c is disposed about the outside of the tube. The sheath does not, however, make direct contact with the tube. Instead, drawsleeve 21 has a first portion 21a disposed within tube 20 between the neck and outlet sections of the sheath and the inner surface of tube 20 and a second portion 21b that extends a substantial distance outwardly from the tube through its second opening at distal end 20b. It will be noted that the combined length of the first and second portions 21a and 21b is substantially greater than the length of tube 20. Specifically, portions 21a and 21b should have a combined length at least 20%, and preferably 25 to 30%, greater than the length of the applicator tube.

The drawsleeve also extends through the opening at the tube's proximal end 20a and includes a reverted third portion 21c that is interposed between the smooth outer surface of the tube 20 and the cylindrical section of the elastic sheath 11. As shown, the third portion 21c is substantially shorter than applicator tube 20. If the third portion of the sheath is provided with a band of pressure-sensitive adhesive 18, the adhesive is preferably covered by a release strip of siliconized paper or other material represented by phantom lines 26 in FIG. 1. The release strip would be peeled away by a user to expose the pressure-sensitive adhesive band before commencing the procedure of applying the sheath to a patient.

If the catheter sheath 11 is provided with an inner sleeve 15 as described and shown, then it has been found advantageous to mount the sheath upon tube 20 (with drawsleeve 21 interposed therebetween) so that the proximal end portion 15a of the sleeve is also everted and is disposed about the outside of tube 20 adjacent the opening at the tube's proximal end 20a. The effect is to stretch or enlarge the proximal end of the sleeve and to reduce the length of that portion of the sleeve disposed within tube 20. Because the distal end portion 15b is thereby positioned at the entrance of the support tube 20, it is exposed in a manner that facilitates fitting the catheter upon a patient as described hereinafter.

FIG. 3 illustrates the catheter/applicator combination as it would be held by a user preparing to apply the catheter to a patient. The second portion 21b of the drawsleeve 21 is firmly gripped between the fingers of one hand and the tube 20 is held between the fingers of the other hand. It has been found that the applicator tube 20 is most effectively supported if the user directly grips the exposed annular portion 20c near the distal end 20b of the tube in the manner illustrated. Alternatively, the applicator tube may be indirectly supported if the user grips a portion of the cylindrical section 11a of the sheath (and/or the exposed end of drawsleeve portion 21c) behind adhesive band 18. The hand that supports the catheter/applicator combination (the left hand shown in FIG. 3) is used to orient the device so that the proximal end 20a of the tube is aligned with the penis and the glans engages the stretched sleeve portion 15b of the sheath (FIG. 4). The other hand (the right hand as shown in FIG. 3) exerts the force required for pulling the drawsleeve and catheter through the interior of tube 20 and, in so doing, everting the cylindrical section 11a of the sheath about the penile shaft of the patient.

It has been found that because of its smooth open-mesh construction, drawsleeve 21 not only slides easily with regard to applicator tube 20 but also is capable of being squeezed into flattened condition, and firmly gripped and retained without slippage, between the fingers of the hand used to extract the drawsleeve from the interior of tube 20. As shown in FIG. 3, the drawsleeve is compliant to the extent that it may be flattened between the thumb and index finger, thereby facilitating a secure, non-slipping relationship between the drawsleeve and the fingers. At the same time, the openness of the mesh reduces the extent of surface contact between the drawsleeve and the outer surface of the tube (and the rounded edges at the proximal end of the tube) to reduce the pulling force required for everting and applying the catheter.

Referring to FIG. 4, drawsleeve 21 is gripped and pulled by one hand in the directions indicated by arrows 30 while tube 20 is supported and advanced by the other hand in the directions represented by arrows 31. As mentioned, the applicator tube may be indirectly supported and advanced by gripping the assembly as represented by dashed arrows 32 and, in that event, forward movement of the fingers towards the proximal end 20a of the tube also contributes to and promotes sliding action between the tube 20 on one hand and the drawsleeve 21 and catheter 11 on the other. In any event, a primary force causing the drawsleeve and catheter to revert and unroll about the penis is the pulling force applied to the drawsleeve and exerted in the direction of arrows 30.

Figure 5:
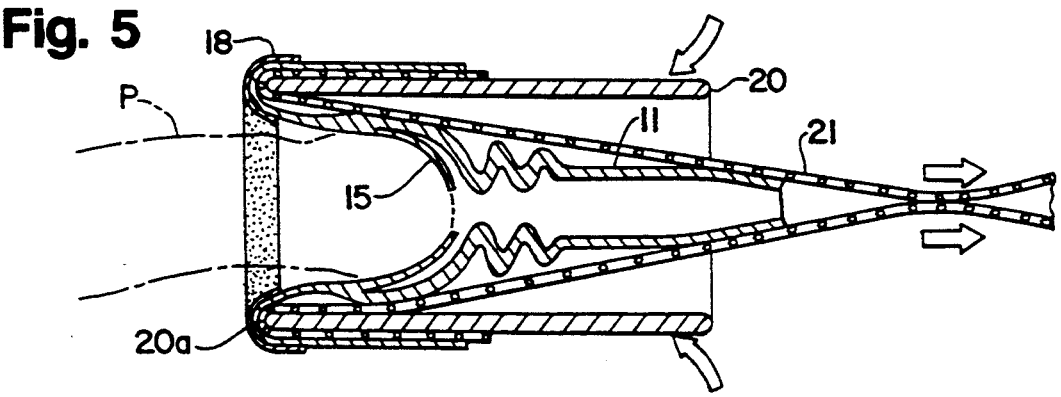
FIG. 5 illustrates an intermediate stage.
Figure 6:
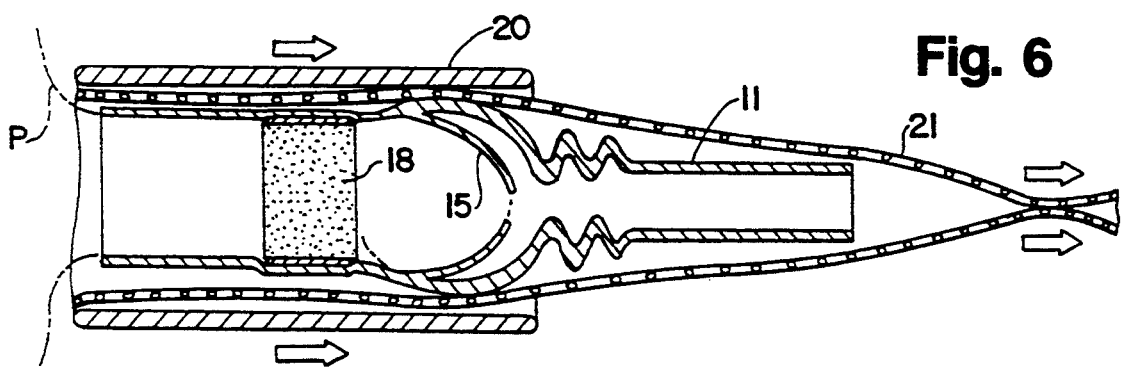
FIG. 6 depicts a final stage with the sheath fully applied.

FIG. 5 illustrates a further stage in the procedure of applying the catheter to a patient, the adhesive band 18 rolling about the rounded proximal edges of tube 20 for contact with the shaft of penis P. In FIG. 6, application of the catheter is complete, and all that remains is for the applicator tube 20 and drawsleeve 21 to be drawn away from the ensheathed penis in the direction represented by arrows 33.

While the applicator tube 20 and drawsleeve 21 of this invention may be used with a catheter that lacks inner sleeve 15, particularly effective results are achieved with a catheter having such a sleeve. The reason is that the stretched distal portion 15b of the sleeve may be brought into direct contact with the end of the penis in the first step of applying the sheath (FIG. 4) and then, as the sheath is reverted and applied, sleeve 15 is pulled and stretched tightly over the glans to form a non-adhesive liquid-tight seal (FIGS. 5 and 6). That seal is then maintained, with the inner sleeve 15 in stretched condition, because of the adhesive contact between band 18 and the penile shaft in an area well behind the glans. In cases where the inner sleeve 15 is omitted, it may be considered necessary or desirable to commence the reverting action without first bringing the sheath into direct contact with the glans because such contact with the relatively thick tapered neck section 11c of the catheter sheath may be undesirable in terms of patient comfort and the elimination of space that would otherwise function as a surge chamber.

While in the foregoing an embodiment of the invention has been disclosed in considerable detail for purposes of illustration, it will be understood by those skilled in the art that many of these details may be varied without departing from the spirit and scope of the invention.

I claim:

1. An external catheter and applicator combination, said catheter comprising a sheath of thin, stretchable, elastic material having a generally cylindrical body section merging at one end with a tapered neck section terminating in an outlet section of reduced diameter; said applicator including a relatively rigid tube having inner and outer surfaces and having oppositely-facing first and second end openings; said tube having a length substantially less than that of said sheath and having an outside diameter slightly greater than the maximum inside diameter of said sheath in an unstretched state; said applicator also including a flexible, tubular, relatively non-stretchable drawsleeve of substantially greater length than each of said tube and said sheath; said sheath having its neck and outlet sections extending axially within said applicator tube; said sheath extending outwardly through said first end opening and being reverted so that said cylindrical body section is disposed about said tube; said drawsleeve having a first portion disposed within the said tube between said neck and outlet sections of said sheath and said inner surface of said tube and having a second portion extending a substantial distance outwardly from said tube through said second opening; said drawsleeve also extending through said first end opening and having a reverted third portion interposed between said outer surface of said tube and said cylindrical body section of said sheath; the frictional resistance between said drawsleeve and said tube being substantially less than the frictional resistance between said drawsleeve and said sheath; whereby, said sheath may be applied to a patient by positioning said tube's first end opening at a glans of a penis and then pulling said second portion of said drawsleeve away from said tube to extract said drawsleeve from the interior of said tube and simultaneously evert and advance the sheath's cylindrical section onto the penile shaft.

2. The combination of claim 1 in which said tube is cylindrical.

3. The combination of claim 1 in which said tube is longer than said cylindrical section of said sheath and is also longer than said third portion of said drawsleeve.

4. The combination of claim 1 in which the combined length of said first and second portions of said drawsleeve exceeds the length of said tube by at least 20%.

5. The combination of claims 1, 2 or 3 in which said cylindrical section of said sheath extending about said third portion of said drawsleeve has an outwardly facing surface; at least a portion of said outwardly facing surface having a pressure-sensitive adhesive coating thereon.

6. The combination of claims 1, 2 or 3 in which said sheath also includes an inner sleeve section disposed within said neck section and exposed at said first end opening of said tube.

7. The combination of claim i in which said tube has an exposed outer surface portion adjacent said second opening for gripping and directing said tube in one hand as said second portion of said drawsleeve is gripped and pulled by the other hand.

8. An external catheter and applicator combination, said catheter comprising a sheath of thin, stretchable, elastic material having a generally cylindrical body section merging at one end with a tapered neck section terminating in an outlet section of reduced diameter; said applicator including a relatively rigid tube having an inner and outer surfaces and having oppositely-facing first and second end openings; said tube having a length substantially less than that of said sheath and having an outside diameter slightly greater than the maximum inside diameter of said sheath in an unstretched state; said applicator also including a flexible drawsleeve of substantially greater length than each of said tube and said sheath and comprising a tubular mesh of intersecting, essentially non-stretchable, polymeric filaments; said sheath having its neck and outlet sections extending axially within said applicator tube, said sheath extending outwardly through said first end opening and being reverted so that said cylindrical body section is disposed about said tube; said drawsleeve having a first portion disposed within said tube between said neck and outlet sections of said sheath and said inner surface of said tube and having a second portion extending a substantial distance outwardly from said tube through said second opening; said drawsleeve also extending through said first end opening and having a reverted third portion interposed between said outer surface of said tube and said cylindrical section of said sheath; the frictional resistance between said drawsleeve and said tube being substantially less than the frictional resistance between said drawsleeve and said sheath; whereby, said sheath may be applied to a patient by positioning said tube's first end opening at a glans of a penis and then pulling said second portion of said drawsleeve away from said tube to extract said drawsleeve from the interior of said tube and simultaneously evert and advance the sheath's cylindrical section onto the penile shaft.

9. The combination of claim 8 in which said tube is cylindrical.

10. The combination of claim 8 in which said tube is longer than said cylindrical section of said sheath and is also longer than said third portion of said drawsleeve.

11. The combination of claim 8 in which the combined length of said first and second portions of said drawsleeve exceeds the length of said tube by at least 20%.

12. The combination of claims 8, 9 or 10 in which said cylindrical section of said sheath extending about said third portion of said drawsleeve has an outwardly facing surface; at least a portion of said outwardly facing surface having a pressure-sensitive adhesive coating thereon.

13. The combination of claims 8, 9 or 10 in which said sheath also includes an inner sleeve section disposed within said neck section and exposed at said first end opening of said tube.

14. The combination of claim 8 in which said tube has an exposed outer surface portion adjacent said second opening for gripping and directing said tube in one hand as said second portion of said drawsleeve is gripped and pulled by the other hand.

15. The combination of claim 8 in which said filaments of said mesh drawsleeve comprise two sets of spaced parallel filaments with the filaments of each set extending in directions that are not parallel with a plane normal to the axis of said applicator tube.

16. The combination of claims 8 or 15 in which said filaments are composed of a polyolefin.

17. A method of applying an external male catheter to the penis of a patient, said catheter comprising a sheath of thin, stretchable, elastic material having a generally cylindrical body section merging at one end with a tapered neck section terminating in an outlet section of reduced diameter; said sheath being supported by a relatively rigid open-ended applicator tube wherein said sheath has its neck and outlet sections axially disposed within said tube and said sheath projects outwardly from one end of said tube where it reverses direction so that said cylindrical body section is everted and disposed externally of said tube; and a friction-reducing drawsleeve having a first portion disposed between the inner surface of said tube and said neck and outlet sections of said sheath and a second portion extending axially from an end of said tube opposite from said one end; said drawsleeve also projecting from said one of said tube and including a third portion interposed between the outer surface of said tube and said cylindrical body section of said sheath; said method comprising the steps of introducing a glans of a penis into the neck section of said sheath at said one end of said tube; then gripping said second portion to extract said drawsleeve from said opposite end of said tube while at the same time urging said tube towards the penis, thereby everting said cylindrical section of said sheath and directing the same onto the penis.

18. The method of claim 17 in which said sheath also includes an inner sleeve section disposed within said neck section and spaced from the inner surface thereof; said step of introducing the glans of the penis into the neck section including the step of urging said sleeve section into direct contact with the glans.

* * * * *